United States Patent
Hsieh (10) Patent No.: US 9,404,784 B2
(45) Date of Patent: Aug. 2, 2016

(54) SURVEILLANCE SYSTEM WITH ELECTRICITY CONVERTING MODULE AND SENSORS AND METHOD THEREOF

(71) Applicant: GEMTEK TECHNOLOGY CO., LTD., Hsinchu (TW)

(72) Inventor: Yun-Cheng Hsieh, Hsinchu (TW)

(73) Assignee: GEMTEK TECHNOLOGY CO., LTD., Hsinchu (TW)

(*) Notice: Subject to any disclaimer, the term of this patent is extended or adjusted under 35 U.S.C. 154(b) by 53 days.

(21) Appl. No.: 14/613,978

(22) Filed: Feb. 4, 2015

(65) Prior Publication Data

US 2016/0011023 A1    Jan. 14, 2016

Related U.S. Application Data

(60) Provisional application No. 62/023,382, filed on Jul. 11, 2014.

(51) Int. Cl.
| F24J 2/00 | (2014.01) |
| G01F 15/06 | (2006.01) |
| G01D 4/00 | (2006.01) |
| G01N 33/18 | (2006.01) |

(52) U.S. Cl.
CPC .............. *G01F 15/063* (2013.01); *G01D 4/00* (2013.01); *G01N 33/18* (2013.01)

(58) Field of Classification Search
USPC .............................. 126/714; 136/205; 290/52
See application file for complete search history.

(56) References Cited

U.S. PATENT DOCUMENTS

| 8,169,101 B2* | 5/2012 | Hinders | F24J 3/085 |
| | | | 290/52 |
| 2014/0020730 A1* | 1/2014 | Imran | H01L 35/30 |
| | | | 136/205 |
| 2014/0202450 A1* | 7/2014 | Doetsch | F24J 2/07 |
| | | | 126/714 |

* cited by examiner

*Primary Examiner* — Jewel V Thompson
(74) *Attorney, Agent, or Firm* — Muncy, Geissler, Olds & Lowe, P.C.

(57) ABSTRACT

A surveillance system with electricity converting module and sensors and method thereof are described. The surveillance system with electricity converting module and sensors and method thereof for converting dynamic energy into electrical energy by the electricity converting module, for sensing at least one status of fluid by the sensors, and for determining whether to issue the at least one status, a charging status and a power status to a remote server wherein the surveillance system and method thereof are used in a fluid transferring apparatus, such as water, oil and/or liquid related devices, to implement the interconnections based on the Internet of Things (IOT). Further, the power supply of the surveillance system becomes self-sufficient advantageously and it is not required to exchange the dry battery in the surveillance system.

23 Claims, 4 Drawing Sheets

SURVEILLANCE SYSTEM WITH ELECTRICITY CONVERTING MODULE AND SENSORS AND METHOD THEREOF

CROSS REFERENCE TO RELATED APPLICATION

This patent application claims priority of U.S. Application Ser. No. 62/023,382, entitled "RECHARGEABLE SENSING APPARATUS FOR DETECTING WATER STATUSES WITH WIRELESS CONTROL MODULE BASED ON INTERNET OF THINGS", which is filed on Jul. 11, 2014, incorporated herein by reference.

BACKGROUND OF THE INVENTION

1. Field of Invention

The present invention relates to a control system, and more particularly to a surveillance system with electricity converting module and sensors and method thereof for converting dynamic energy into electrical energy by the electricity converting module, for sensing at least one status of fluid by the sensors, and for determining whether to issue the at least one status, a charging status and a power status to a remote server wherein the surveillance system and method thereof are used in a fluid transferring apparatus, such as water, oil and/or liquid related devices, to implement the interconnections based on the Internet of Things (IOT).

2. Description of Prior Art

Conventionally, a sensor for detecting water quality and quantity with manual operation is time-consuming and spends a lot of human resources. For example, the maintenance personnel need to manually detect the detecting water quality and quantity of the water flowing the water pipelines using an instrument on the scene. Consequently, there is a need to develop a system for detecting water quality and quantity based on the Internet of Things (IOT) to solve the aforementioned problem.

SUMMARY OF THE INVENTION

One objective of the present invention is to provide a surveillance system with electricity converting module and sensors and method thereof for converting dynamic energy into electrical energy by the electricity converting module, for sensing at least one status of fluid by the sensors, and for determining whether to issue the at least one status, the charging status and the power status to a remote server in order to remotely and instantly notify the mobile intelligent devices and/or maintenance personnel of these statuses. Further, the power supply of the surveillance system becomes self-sufficient advantageously and it is not required to exchange the dry battery in the surveillance system.

According to the above objective, the present invention sets forth a surveillance system. The surveillance system comprises at least one sensor coupled to a fluid transferring apparatus, for sensing at least one status of fluid wherein the fluid flows through the fluid transferring apparatus; an electricity converting module coupled to the fluid transferring apparatus, for converting dynamic energy of the fluid into electrical energy when the fluid flows through the electricity converting module; a power module coupled to the electricity converting module, for storing the electrical energy from the electricity converting module; and a control module coupled to the at least one sensor, the electricity converting module and the power module respectively, for managing the at least one sensor to process the at least one status of the fluid, for controlling the electricity converting module, and for manipulating the power module to supply the stored electrical energy to the at least one sensor and the control module respectively.

In one embodiment, the at least one sensor is a flow sensor comprising a flow driving device disposed in the fluid transferring apparatus, for generating a circular motion at a rotating speed when the fluid flows through the flow driving device wherein the rotating speed of the flow driving device is positively related to a flow rate of the at least one status; and a flow rate detecting device disposed on an outer surface of the fluid transferring apparatus, detecting the rotating speed of the flow driving device for sending the flow rate of the at least one status to the control module.

In one embodiment, the control module coupled to the flow rate detecting device is capable of computing a fluid quantity flowing through the fluid transferring apparatus based on the flow rate during a predetermined time interval.

In one embodiment, the at least one sensor is a total dissolved solid (TDS) sensor disposed in the fluid transferring apparatus, for detecting a TDS status of the at least one status to send the TDS status to the control module.

In one embodiment, the control module coupled to the TDS sensor is capable of determining whether the TDS status exceeds a predetermined value.

In one embodiment, the electricity converting module further comprises a dynamic energy generating device installed with a plurality of permanent magnets in the fluid transferring apparatus and coupled to a conduction coil on an outer surface of the fluid transferring apparatus, for generating the electrical energy when the fluid flows through the dynamic energy generating device wherein the conduction coil regenerates the electrical energy by magnetic flux change between the permanent magnets and the conduction coil if the permanent magnets rotate in relation to the conduction coil; and an electrical energy outputting device coupled to the dynamic energy generating device, for receiving the regenerated electrical energy and outputting the regenerated electrical energy to the power module.

In one embodiment, the power module receives the electrical energy to charge a rechargeable battery and issues a charging status and a power status of remaining power in the rechargeable battery to the control module.

In one embodiment, the control module determines whether to issue the at least one status of the fluid, the charging status and the power status of the remaining power to a remote server.

In one embodiment, the control module further comprises a controller coupled to the at least one sensor, the electricity converting module and the power module, for controlling operations of the at least one sensor, the electricity converting module and the power module; a timer coupled to the controller, for evaluating usage time of the surveillance system in order to remind a user to change the surveillance system based on the usage time; and a wireless transceiver coupled to the controller, for either transmitting the at least one status to a remote server or receiving a control instruction from the remote server.

In one embodiment, the at least one sensor and the electricity converting module employ a dynamic energy generating device disposed in the fluid transferring apparatus, for generating a circular motion at a rotating speed and regenerating the electrical energy when the fluid flows through the dynamic energy generating device.

In one embodiment, the rotating speed of the flow driving device is positively related to a flow rate of the at least one status.

In one embodiment, the dynamic energy generating device is installed with a plurality of permanent magnets in the fluid transferring apparatus and couples to a conduction coil to allow the conduction coil to regenerate the electrical energy by magnetic flux change between the permanent magnets and the conduction coil if the permanent magnets rotate in relation to the conduction coil.

According to the above objective, the present invention sets forth a surveillance method. The surveillance method comprises the steps of: sensing at least one status of fluid by way of at least one sensor wherein the fluid flows through a fluid transferring apparatus; converting dynamic energy of the fluid into electrical energy by way of an electricity converting module when the fluid flows through the electricity converting module; storing the electrical energy from the electricity converting module by way of a power module; managing the at least one sensor to process the at least one status of the fluid by way of a control module; controlling the electricity converting module; and manipulating the power module by way of the control module for supplying the stored electrical energy to the at least one sensor and the control module respectively.

In one embodiment, during the step of sensing the at least one status of the fluid by way of the at least one sensor wherein the fluid flows through a fluid transferring apparatus, further comprising the steps of: generating a circular motion at a rotating speed by way of a flow driving device when the fluid flows through the flow driving device wherein the rotating speed of the flow driving device is positively related to a flow rate of the at least one status; detecting the rotating speed of the flow driving device by way of a flow rate detecting device; and sending the flow rate of the at least one status to the control module by way of the flow rate detecting device.

In one embodiment, during the step of sensing the at least one status of the fluid by way of the at least one sensor wherein the fluid flows through a fluid transferring apparatus, further comprising a step of: computing a fluid quantity flowing through the fluid transferring apparatus based on the flow rate during a predetermined time interval.

In one embodiment, the surveillance method further comprises the steps of: detecting a TDS status of the at least one status by way of a TDS sensor; and sending the TDS status to the control module by way of the TDS sensor.

In one embodiment, during the step of detecting the TDS status of the at least one status by way of the TDS sensor, further comprising a step of: determining whether the TDS status exceeds a predetermined value by way of the control module.

In one embodiment, during the step of converting the dynamic energy of the fluid into electrical energy by way of the electricity converting module when the fluid flows through the electricity converting module, further comprising the steps of: generating the electrical energy when the fluid flows through the dynamic energy generating device wherein a conduction coil regenerates the electrical energy by magnetic flux change between the permanent magnets and the conduction coil if the permanent magnets rotate in relation to the conduction coil; and receiving the electrical energy for outputting the electrical energy to the power module by way of an electrical energy outputting device.

In one embodiment, during the step of storing the electrical energy from the electricity converting module by way of the power module, further comprising the steps of: charging a rechargeable battery by the electrical energy from the electricity converting module by way of the power module; and issuing a charging status and a power status of remaining power in the rechargeable battery to the control module by way of the power module.

In one embodiment, during the step of charging the rechargeable battery by the electrical energy from the electricity converting module, further comprising a step of: determining whether to issue the at least one status of the fluid, the charging status and the power status of the remaining power to a remote server by way of the control module.

In one embodiment, during the step of managing the at least one sensor to process the at least one status of the fluid by way of the control module, further comprising the steps of: controlling operations of the at least one sensor, the electricity converting module and the power module; evaluating usage time of the surveillance system by way of a timer in order to remind a user to change the surveillance system based on the usage time; and either transmitting the at least one status to a remote server or receiving a control instruction from the remote server by way of a wireless transceiver.

In one embodiment, during the steps of sensing at least one status of fluid by way of at least one sensor wherein the fluid flows through a fluid transferring apparatus and converting dynamic energy of the fluid into electrical energy by way of an electricity converting module when the fluid flows through the electricity converting module, further comprising a step of: generating a circular motion at a rotating speed and regenerating the electrical energy when the fluid flows through the dynamic energy generating device.

In one embodiment, the rotating speed of the dynamic energy generating device is positively related to a flow rate of the at least one status.

DETAILED DESCRIPTION OF THE PREFERRED EMBODIMENTS

Figure 1:
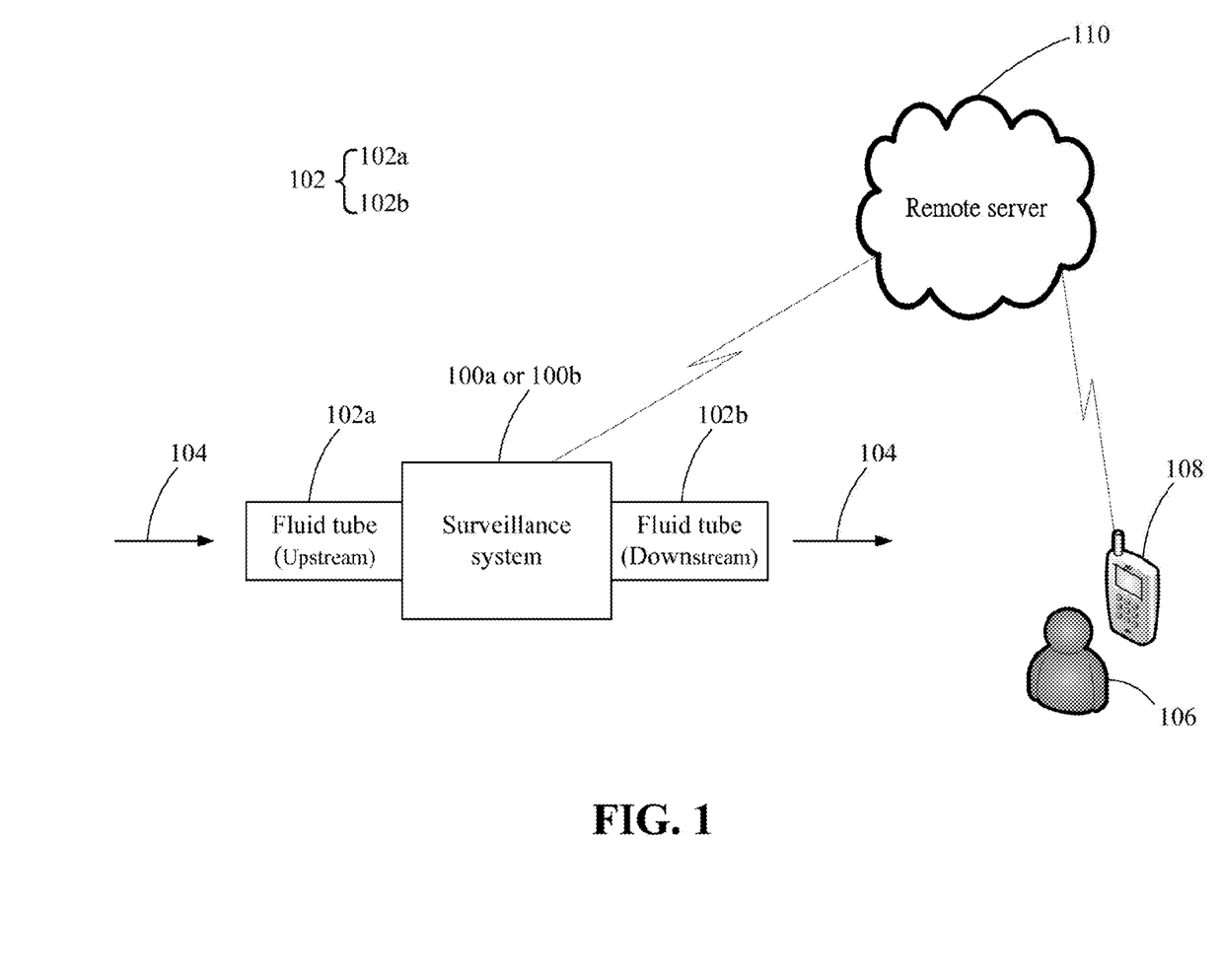
FIG. 1 is a schematic view of a surveillance system for converting electrical energy, sensing at least one status and processing the at least one status to the mobile intelligent devices via a remote server based on the Internet of Things (IOT) according to one embodiment of the present invention.

Referring to FIG. 1, it is a schematic view of a surveillance system 100*a*, 100*b* for converting electrical energy, sensing at least one status and processing the at least one status to the mobile intelligent device 108 via a remote server 110 to implement the interconnections based on the Internet of Things (IOT) according to one embodiment of the present invention.

The surveillance system 100*a*, 100*b* is disposed between the upstream section 102*a* and the downstream section 102*b* of the fluid transferring apparatus 102, e.g. water tube, for converting dynamic energy into electrical energy, for sensing at least one status, e.g. water quality and water quantity of fluid flowing through the fluid transferring apparatus 102, the usage time of the surveillance system 100a, 100b, and the battery electric power status, and for processing the at least one status to the mobile intelligent device 108 via a remote server 110. In one embodiment, the surveillance system 100a, 100b is installed with the fluid transferring apparatus 102, e.g. water drinking dispenser or water filter, disposed in the upstream section 102a along the flow path 104 for detecting the statuses, e.g. water quality and water quantity, to determine whether the water characteristics exceed one or more predetermined threshold, such as total water quantity, total dissolved solid (TDS) value and/or the usage time of the surveillance system 100a, 100b exceeds its life span. In one case, the fluid transferring apparatus 102 may be a section of fluid pipeline.

In FIG. 1, the maintenance personnel 106 employ a mobile intelligent device 108 installed with an application program therein to acquire the information of the water statuses or to operate the surveillance system 100a, 100b by way of a wireless transmission manner via a remote server 110. In other words, the surveillance system 100a, 100b is capable of uploading the information of the water statuses to the remote server 110 so that the maintenance personnel 106 are able to access the updated information of the water statuses remotely and instantly. Further, the mobile intelligent device 108 sends the operation instructions to control the surveillance system 100a, 100b for configuring the surveillance system 100a, 100b to report the mobile intelligent device 108 of the water quality and water quantity, the usage time of the surveillance system, and the battery electric power status periodically. Thus, the maintenance personnel 106 effectively decide whether the fluid transferring apparatus 102 should be replaced by a new one.

Figure 2:
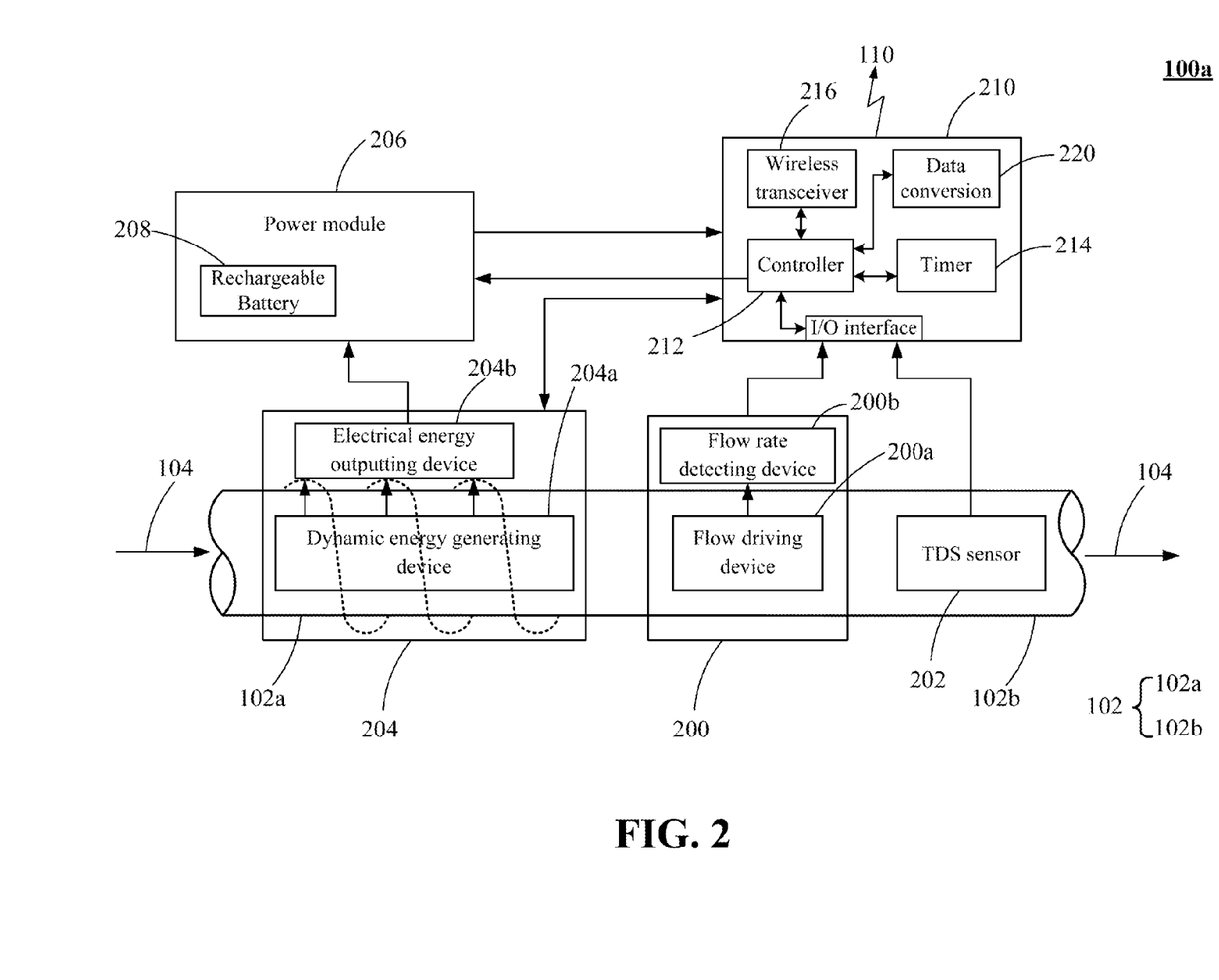
FIG. 2 is a detailed schematic view of the surveillance system for converting electrical energy by electricity converting module, sensing at least one status and processing the at least one status by control module according to first embodiment of the present invention.

Referring to FIG. 2, it is a detailed schematic view of the surveillance system 100a for converting electrical energy by electricity converting module 204, sensing at least one status by sensors 200, 202 and processing the at least one status by control module 210 according to first embodiment of the present invention. The surveillance system 100a comprises at least one sensor, e.g. flow sensor 200 and TDS sensor 202, an electricity converting module 204, a power module 206 with a rechargeable battery 208, and a control module 210. In one embodiment, the flow sensor 200 and electricity converting module 204 are operated independently.

The flow sensor 200 and TDS sensor 202 respectively of the sensors are coupled to the control module 210. The electricity converting module 204 is coupled to the power module 206 and control module 210. The power module 206 is coupled to the control module 210. The flow sensor 200 includes a flow driving device 200a and a flow rate detecting device 200b coupled to the flow driving device 200a. The electricity converting module 204 includes a dynamic energy generating device 204a and electrical energy outputting device 204b coupled to the dynamic energy generating device 204a. The control module 210 further comprises a controller 212, a timer 214, a wireless transceiver 216, an input/output (I/O) interface 218 and a data conversion 220. The controller 212 is coupled to the timer 214, the wireless transceiver 216, the I/O interface 218 and the data conversion 220.

In FIG. 2, the at least one sensor coupled to a fluid transferring apparatus 102 senses at least one status of fluid wherein the fluid flows through the fluid transferring apparatus 102. In one embodiment of flow sensor of the sensor, the flow driving device 202a disposed in the fluid transferring apparatus 102 generates a circular motion at a rotating speed when the fluid flows through the flow driving device 202a wherein the rotating speed of the flow driving device 202a is positively related to a flow rate of the at least one status. The flow rate detecting device 200b disposed on an outer surface of the fluid transferring apparatus 102 detects the rotating speed of the flow driving device 200a for sending the flow rate of the at least one status to the control module 210. In one case, the control module 210 coupled to the flow rate detecting device 200b is capable of computing a fluid quantity flowing through the fluid transferring apparatus 102 based on the flow rate during a predetermined time interval so that the control module 210 calculates the fluid consumption at any time.

Specifically, the flow sensor 200 is used to sense the water flow rate of the water tube 102a, 102b and correspondingly sends the flow rate data to the control module 210 to be processed. In one embodiment, if the total quantity of the fluid transferring apparatus exceeds a predetermined threshold, e.g. ten thousands liters but not limited, which flows through the flow sensor 200 based on the computation result of the flow rate, the control module 210 receives the computation result and indicates the fluid transferring apparatus need to be changed by the maintenance personnel 106. In one preferred embodiment, the flow driving device 200a of flow sensor 200 serves as a fan having leaf blade and installed with at least one permanent magnet. When the water flows to the fan, the fan with the leaf blade rotates and makes the permanent magnets (not shown) to form a circular motion. The flow rate detecting device 200b, e.g. either magnetism reed switch or a Hall effect integrated circuit (IC), is used to sense the permanent magnets whether the magnetism reed switch or Hall effect IC is attracted by the permanent magnets repeatedly to be a short circuit or not. Thus, the magnetism reed switch or Hall effect IC indicates "ON" ("1") or "OFF" ("0") status. The controller 212 analyzes the changed frequency of the "ON" ("1") or "OFF" ("0") status to acquire the revolution times which are positively related to the flow rate of the water in the water tube and thus to generate the flow rate data.

In another embodiment, the sensor is a total dissolved solid (TDS) sensor 202 disposed in the fluid transferring apparatus 102, for detecting a TDS status of the at least one status to send the TDS status to the control module 210. The TDS sensor 202 is employed to detect the solid material quantity dissolved in the water and to sense the turbidity and/or impurity of the water for transmitting TDS data to the control module 210. In one case, if the control module 210 determines whether the TDS status exceeds a predetermined concentration value, e.g. 40 ppm (parts per million) or 500 mg/L (milligram per liter), which flow through the TDS sensor 202 based on the computation result of the TDS, the control module 210 indicates that the fluid transferring apparatus 102, e.g. filter element, need to be repaired or replaced.

As shown in FIG. 2, the electricity converting module 204 coupled to the fluid transferring apparatus 102 converts dynamic energy of the fluid into electrical energy when the fluid flows through the electricity converting module 204. In one embodiment of the electricity converting module 204, a dynamic energy generating device 204a installed with a plurality of permanent magnets in the fluid transferring apparatus 102 and coupled to a conduction coil on an outer surface of the fluid transferring apparatus 102, for generating the electrical energy when the fluid flows through the dynamic energy generating device 204a wherein the conduction coil regenerates the electrical energy by magnetic flux change between the permanent magnets and the conduction coil if the permanent magnets rotate in relation to the conduction coil.

Further, an electrical energy outputting device 204b coupled to the dynamic energy generating device 204a receives the regenerated electrical energy and outputs the regenerated electrical energy to the power module 206. In one preferred embodiment, the dynamic energy generating device 204a of the dynamic and electricity converting module 204 serves as a fan having leaf blade and installed with at least one permanent magnet. When the water flows to the fan, the fan with the leaf blade rotates and makes the permanent magnets (not shown) to form a circular motion so that external conduction coils outside the water tube 102a, 102b generates electrical energy due to the changed magnetic field to be provided to the power module 206.

In FIG. 2, the power module 206 coupled to the electricity converting module 204 stores the electrical energy from the electricity converting module 204. The power module 206 receives the electrical energy to charge a rechargeable battery 208 and issues a charging status and a power status of remaining power in the rechargeable battery 208 to the control module 210. The control module 210 determines whether to issue the at least one status of the fluid, the charging status and the power status of the remaining power to a remote server 110, e.g. cloud server. In addition, the dynamic and electricity converting module 204 converts the dynamic energy of the water flow in the water tube 102a, 102b into electrical energy and the power module 206 stores the electrical energy to the battery 208 of the power module 206 so that the battery 206 provides the energy to the control module 210 for operating the surveillance system 100a. Thus, the power consumption of the surveillance system 100a is decreased advantageously and it is not required to exchange the battery 208. Specifically, the power module 206 receives the electrical energy from the electrical energy outputting device 204b, e.g. external conduction coils and charges the battery 208. Further, the controller 212 controls the power module 206 not to charge the battery 208 when the power status of the battery 208 is higher. The controller 212 controls the power module 206 to charge the battery 208 when the power status of the battery 208 is lower and the lower power status is only supplied to the controller 212 and the flow sensor 200, TDS sensor 202 and the dynamic and electricity converting module 204 and the data are not transmitted to the remote server 110 until the battery 208 is in higher power status.

The control module 210 manages the at least one sensor to process the at least one status of the fluid, controls the electricity converting module, and manipulates the power module 206 to supply the stored electrical energy to the at least one sensor and the control module 210 respectively. In the control module 210, a controller 212 coupled to the at least one sensor, the electricity converting module 204 and the power module 206 controls operations of the at least one sensor, the electricity converting module 204 and the power module 206. Further, the controller 212 of the control module 210 is employed to control the acquisition of the flow rate data, TDS data and usage time of the surveillance system corresponding to the flow sensor 200, TDS sensor 202 and timer 214. In other words, the controller 212 is capable of processing the acquisition data. Further, the control module 210 performs a handshaking operation with the remote server 110 for uploading the acquisition data of the fluid transferring apparatus to the remote server 110 so that the maintenance personnel 106 can decide whether the fluid transferring apparatus 102 need to be replaced after the mobile intelligent device, e.g. phone cell 108, acquires the water statuses of the fluid transferring apparatus. I/O interface 218, e.g. general purpose I/O (GPIO), is a transmission channel of the sensing data from the sensors 200, 202 to the control module 210. The data conversion 220 is used to convert the sensing data from one type, e.g. analog formats of TDS status and flow rate, to other type, e.g. digital format of wireless transceiver, or vice versa.

The timer 214 of the control module 210 coupled to the controller evaluates usage time of the surveillance system 100a in order to remind a user to replace the fluid transferring apparatus 102 by a new one based on the usage time. For example, if the surveillance system 100a is utilized beyond six months, the control module 210 indicates the fluid transferring apparatus 102, e.g. filter element need to be replaced.

The wireless transceiver 216 coupled to the controller 212 either transmits the at least one status to a remote server 110 or receives a control instruction from the mobile intelligent device 108 via the remote server 110. The wireless transceiver 216, e.g. Wi-Fi module, ZigBee, Z-wave, Sub-Ghz, proprietary RF serves to transmit data to the remote server 110 or receive control instructions from remote server 110. ZigBee is a specification for a suite of high level communication protocols used to create personal area networks built from small, low-power digital radios. ZigBee is based on an IEEE 802.15 standard. Z-Wave is a wireless communications protocol designed for home automation, specifically to remotely control applications in residential and light commercial environments. Specifically, the controller 212, the timer 214 and wireless transceiver 216 are integrated into an assembly module for downsizing the surveillance system 100a, 100b and save the manufacturing cost of the surveillance system 100a. In one embodiment, if the flow sensor 200, the TDS sensor 202 and the timer 214 do not generate the data of water statuses for a long time, the wireless transceiver 216 of the control module 210 transmits an alarm message to the remote server 110 to notify the mobile intelligent devices 108 corresponding to the maintenance personnel 106 via the mobile intelligent device 108 for ensuring whether the flow sensor 200, the TDS sensor 202 and the timer 214 are abnormal or not.

Figure 3:
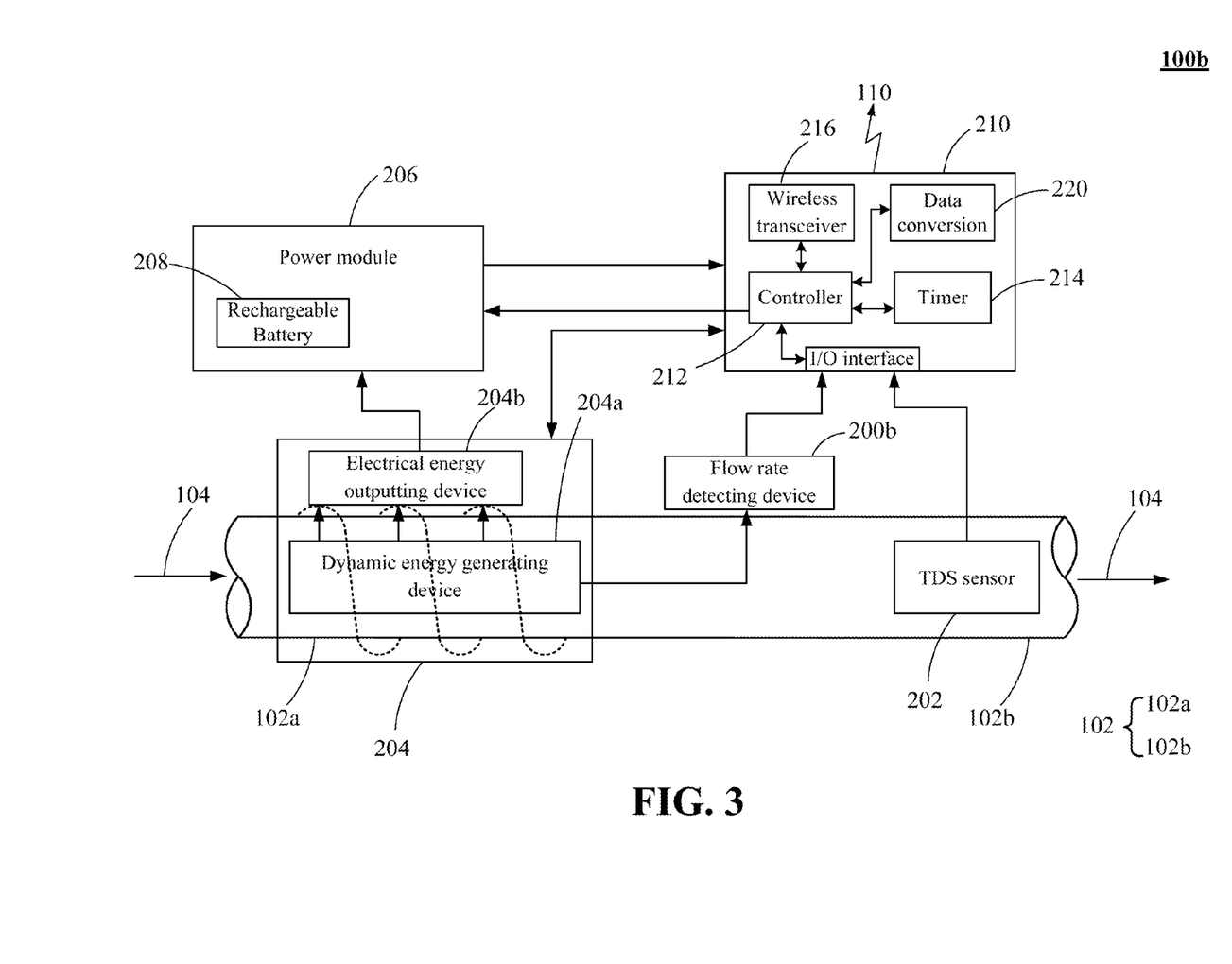
FIG. 3 is a detailed schematic view of the surveillance system for converting electrical energy by electricity converting module, sensing at least one status and processing the at least one status by control module according to second embodiment of the present invention.

Referring to FIG. 3, it is a detailed schematic view of the surveillance system 100b for converting electrical energy by electricity converting module 204, sensing at least one status and processing the at least one status by control module 210 according to second embodiment of the present invention. The surveillance system 100b is similar to surveillance system 100a in FIG. 2. The difference is that the flow driving device 200a and the dynamic energy generating device 204a of the electricity converting module 204 simultaneously employs the same fan having leaf blade and installed with at least one permanent magnet to save the manufacturing cost of the surveillance system 100b. In other words, the at least one sensor and the electricity converting module 204 employ a dynamic energy generating device 204a disposed in the fluid transferring apparatus 102 for generating a circular motion at a rotating speed and regenerating the electrical energy when the fluid flows through the dynamic energy generating device 204a. In one preferred embodiment, the rotating speed of the dynamic energy generating device 204a is positively related to a flow rate of the at least one status. In one case, the dynamic energy generating device 204a is installed with a plurality of permanent magnets in the fluid transferring apparatus 102 and couples to a conduction coil to allow the conduction coil to regenerate the electrical energy by magnetic flux change between the permanent magnets and the conduction coil if the permanent magnets rotate in relation to the conduction coil.

Figure 4:
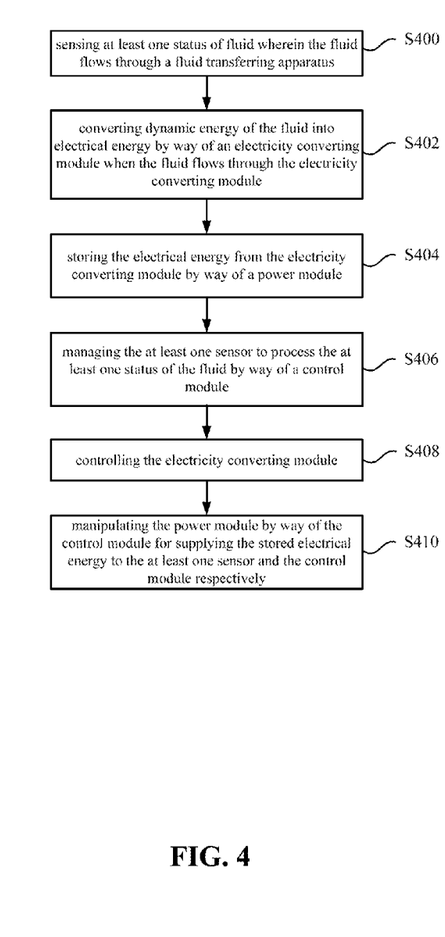
FIG. 4 is a flow chart of a surveillance method for converting electrical energy by electricity converting module, sensing at least one status and processing the at least one status by control module according to one embodiment of the present invention.

Please refer to FIG. 1 through FIG. 4. FIG. 4 is a flow chart of a surveillance method for converting electrical energy by electricity converting module 204, sensing at least one status and processing the at least one status by control module 210 according to one embodiment of the present invention. The surveillance method includes the following steps.

In step S400, at least one sensor senses at least one status of fluid wherein the fluid flows through a fluid transferring apparatus 102. In one embodiment, the flow driving device 200a generates a circular motion at a rotating speed when the fluid flows through the flow driving device 200a wherein the rotating speed of the flow driving device 200b is positively related to a flow rate of the at least one status. The flow rate detecting device 200b detects the rotating speed of the flow driving device 200a and sends the flow rate of the at least one status to the control module 210. The control module 210 computes a fluid quantity flowing through the fluid transferring apparatus 102 based on the flow rate during a predetermined time interval so that the control module 210 calculates the fluid consumption at any time. In another embodiment, the TDS sensor 102 detects a TDS status of the at least one status and sends the TDS status to the control module 210 so that the control module 210 is capable of determining whether the TDS status exceeds a predetermined value.

In step S402, electricity converting module 204 converts dynamic energy of the fluid into electrical energy when the fluid flows through the electricity converting module 204. In one embodiment, the dynamic energy generating device 204a generates the electrical energy when the fluid flows through the dynamic energy generating device 204a wherein a conduction coil regenerates the electrical energy by magnetic flux change between the permanent magnets and the conduction coil if the permanent magnets rotate in relation to the conduction coil. The electrical energy outputting device 204b receives the electrical energy for outputting the electrical energy to the power module 206.

Still in another embodiment, during the step S400 of sensing at least one status of fluid by way of at least one sensor wherein the fluid flows through a fluid transferring apparatus 102 and during the step S402 of converting dynamic energy of the fluid into electrical energy by way of an electricity converting module 204 when the fluid flows through the electricity converting module 204, the dynamic energy generating device 204a generates a circular motion at a rotating speed and regenerating the electrical energy when the fluid flows through the dynamic energy generating device 204a wherein the rotating speed of the dynamic energy generating device is positively related to a flow rate of the at least one status.

In step S404, a power module 206 stores the electrical energy from the electricity converting module 204. In one embodiment, the power module 210 charges a rechargeable battery 208 by the electrical energy from the electricity converting module 204. The power module 206 issues a charging status and a power status of remaining power in the rechargeable battery 208 to the control module 210. The control module 210 determines whether to issue the at least one status of the fluid, the charging status and the power status of the remaining power to a remote server 110.

In step S406, a control module 210 manages the at least one sensor to process the at least one status of the fluid. In one embodiment, the controller 212 of the control module 210 controls operations of the at least one sensor, the electricity converting module 204 and the power module 206. The timer 214 of the control module 210 evaluates usage time of a surveillance system 100a, 100b in order to remind a user to replace the fluid transferring apparatus 102 by a new one based on the usage time. The wireless transceiver 216 of the control module 210 either transmitting the at least one status to a remote server 110 or receiving a control instruction from the remote server 110.

In step S408, the control module 210 controls the electricity converting module 204 to detect whether electricity converting module 204 implements the converting dynamic energy of the fluid into electrical energy.

In step S410, the control module 210 manipulates the power module 206 for supplying the stored electrical energy to the at least one sensor 200, 202 and the control module 210 respectively.

According to above-mentioned descriptions, the present invention employs a surveillance system with electricity converting module and sensors and method thereof for converting dynamic energy into electrical energy by the electricity converting module, for sensing at least one status of fluid by the sensors, and for determining whether to issue the at least one status, the charging status, the usage time of the surveillance system, and the power status to a remote server in order to remotely and instantly notify the mobile intelligent devices and/or maintenance personnel of these statuses. Further, the power supply of the surveillance system becomes self-sufficient advantageously and it is not required to exchange the dry battery in the surveillance system.

As is understood by a person skilled in the art, the foregoing preferred embodiments of the present invention are illustrative rather than limiting of the present invention. It is intended that they cover various modifications and similar arrangements be included within the spirit and scope of the present invention, the scope of which should be accorded the broadest interpretation so as to encompass all such modifications and similar structure.

What is claimed is:

1. A surveillance system, comprising:
   at least one sensor coupled to a fluid transferring apparatus, for sensing at least one status of fluid wherein the fluid flows through the fluid transferring apparatus;
   an electricity converting module coupled to the fluid transferring apparatus, for converting dynamic energy of the fluid into electrical energy when the fluid flows through the electricity converting module;
   a power module coupled to the electricity converting module, for storing the electrical energy from the electricity converting module; and
   a control module coupled to the at least one sensor, the electricity converting module and the power module respectively, for managing the at least one sensor to process the at least one status of the fluid, for controlling the electricity converting module, and for manipulating the power module to supply the stored electrical energy to the at least one sensor and the control module respectively.

2. The surveillance system of claim 1, wherein the at least one sensor is a flow sensor comprising:
   a flow driving device disposed in the fluid transferring apparatus, for generating a circular motion at a rotating speed when the fluid flows through the flow driving device wherein the rotating speed of the flow driving device is positively related to a flow rate of the at least one status; and
   a flow rate detecting device disposed on an outer surface of the fluid transferring apparatus, detecting the rotating speed of the flow driving device for sending the flow rate of the at least one status to the control module.

3. The surveillance system of claim 2, wherein the control module coupled to the flow rate detecting device is capable of computing a fluid quantity flowing through the fluid transferring apparatus based on the flow rate during a predetermined time interval.

4. The surveillance system of claim 1, wherein the at least one sensor is a total dissolved solid (TDS) sensor disposed in the fluid transferring apparatus, for detecting a TDS status of the at least one status to send the TDS status to the control module.

5. The surveillance system of claim 4, wherein the control module coupled to the TDS sensor is capable of determining whether the TDS status exceeds a predetermined value.

6. The surveillance system of claim 1, wherein the electricity converting module further comprises:
a dynamic energy generating device installed with a plurality of permanent magnets in the fluid transferring apparatus and coupled to a conduction coil on an outer surface of the fluid transferring apparatus, for generating the electrical energy when the fluid flows through the dynamic energy generating device wherein the conduction coil regenerates the electrical energy by magnetic flux change between the permanent magnets and the conduction coil if the permanent magnets rotate in relation to the conduction coil; and
an electrical energy outputting device coupled to the dynamic energy generating device, for receiving the regenerated electrical energy and outputting the regenerated electrical energy to the power module.

7. The surveillance system of claim 1, wherein the power module receives the electrical energy to charge a rechargeable battery and issues a charging status and a power status of remaining power in the rechargeable battery to the control module.

8. The surveillance system of claim 7, wherein the control module determines whether to issue the at least one status of the fluid, the charging status and the power status of the remaining power to a remote server.

9. The surveillance system of claim 1, wherein the control module further comprises:
a controller coupled to the at least one sensor, the electricity converting module and the power module, for controlling operations of the at least one sensor, the electricity converting module and the power module;
a timer coupled to the controller, for evaluating usage time of the surveillance system in order to remind a user to change the surveillance system based on the usage time; and
a wireless transceiver coupled to the controller, for either transmitting the at least one status to a remote server or receiving a control instruction from the remote server.

10. The surveillance system of claim 1, wherein the at least one sensor and the electricity converting module employ a dynamic energy generating device disposed in the fluid transferring apparatus, for generating a circular motion at a rotating speed and regenerating the electrical energy when the fluid flows through the dynamic energy generating device.

11. The surveillance system of claim 10, wherein the rotating speed of the dynamic energy generating device is positively related to a flow rate of the at least one status.

12. The surveillance system of claim 10, wherein the dynamic energy generating device is installed with a plurality of permanent magnets in the fluid transferring apparatus and couples to a conduction coil to allow the conduction coil to regenerate the electrical energy by magnetic flux change between the permanent magnets and the conduction coil if the permanent magnets rotate in relation to the conduction coil.

13. A surveillance method, comprising the steps of:
sensing at least one status of fluid by way of at least one sensor wherein the fluid flows through a fluid transferring apparatus;
converting dynamic energy of the fluid into electrical energy by way of an electricity converting module when the fluid flows through the electricity converting module;
storing the electrical energy from the electricity converting module by way of a power module;
managing the at least one sensor to process the at least one status of the fluid by way of a control module;
controlling the electricity converting module; and
manipulating the power module by way of the control module for supplying the stored electrical energy to the at least one sensor and the control module respectively.

14. The surveillance method of claim 13, during the step of sensing the at least one status of the fluid by way of the at least one sensor wherein the fluid flows through a fluid transferring apparatus, further comprising the steps of:
generating a circular motion at a rotating speed by way of a flow driving device when the fluid flows through the flow driving device wherein the rotating speed of the flow driving device is positively related to a flow rate of the at least one status;
detecting the rotating speed of the flow driving device by way of a flow rate detecting device; and
sending the flow rate of the at least one status to the control module by way of the flow rate detecting device.

15. The surveillance method of claim 14, during the step of sensing the at least one status of the fluid by way of the at least one sensor wherein the fluid flows through the fluid transferring apparatus, further comprising a step of: computing a fluid quantity flowing through the fluid transferring apparatus based on the flow rate during a predetermined time interval by way of the control module.

16. The surveillance method of claim 13, further comprising the steps of:
detecting a TDS status of the at least one status by way of a TDS sensor; and
sending the TDS status to the control module by way of the TDS sensor.

17. The surveillance method of claim 16, during the step of detecting the TDS status of the at least one status by way of the TDS sensor, further comprising a step of:
determining whether the TDS status exceeds a predetermined value by way of the control module.

18. The surveillance method of claim 13, during the step of converting the dynamic energy of the fluid into electrical energy by way of the electricity converting module when the fluid flows through the electricity converting module, further comprising the steps of:
generating the electrical energy when the fluid flows through a dynamic energy generating device wherein a conduction coil regenerates the electrical energy by magnetic flux change between the permanent magnets and the conduction coil if the permanent magnets rotate in relation to the conduction coil; and
receiving the electrical energy for outputting the electrical energy to the power module by way of an electrical energy outputting device.

19. The surveillance method of claim 13, during the step of storing the electrical energy from the electricity converting module by way of the power module, further comprising the steps of:
charging a rechargeable battery by the electrical energy from the electricity converting module by way of the power module; and
issuing a charging status and a power status of remaining power in the rechargeable battery to the control module by way of the power module.

20. The surveillance method of claim 19, during the step of charging the rechargeable battery by the electrical energy from the electricity converting module, further comprising a step of: determining whether to issue the at least one status of the fluid, the charging status and the power status of the remaining power to a remote server by way of the control module.

21. The surveillance method of claim 13, during the step of managing the at least one sensor to process the at least one status of the fluid by way of the control module, further comprising the steps of:
controlling operations of the at least one sensor, the electricity converting module and the power module;
evaluating usage time of a surveillance system by way of a timer in order to remind a user to change the surveillance system based on the usage time; and
either transmitting the at least one status to a remote server or receiving a control instruction from the remote server by way of a wireless transceiver.

22. The surveillance method of claim 13, during the steps of sensing at least one status of fluid by way of at least one sensor wherein the fluid flows through a fluid transferring apparatus and converting dynamic energy of the fluid into electrical energy by way of an electricity converting module when the fluid flows through the electricity converting module, further comprising a step of:
generating a circular motion at a rotating speed and regenerating the electrical energy when the fluid flows through a dynamic energy generating device.

23. The surveillance method of claim 22, wherein the rotating speed of the dynamic energy generating device is positively related to a flow rate of the at least one status.

* * * * *